(12) United States Patent
Mukherjee et al.

(10) Patent No.: US 11,478,778 B2
(45) Date of Patent: *Oct. 25, 2022

(54) MIXED METAL OXIDE CATALYST USEFUL FOR PARAFFIN DEHYDROGENATION

(71) Applicant: Exelus Inc., Fairfield, NJ (US)

(72) Inventors: Mitrajit Mukherjee, Fairfield, NJ (US); Vamsi M. Vadhri, Fairfield, NJ (US); Narendra Joshi, Fairfield, NJ (US); Grace Brock, Fairfield, NJ (US)

(73) Assignee: Exelus Inc., Fairfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/331,539

(22) Filed: May 26, 2021

(65) Prior Publication Data

US 2021/0346868 A1 Nov. 11, 2021

Related U.S. Application Data

(63) Continuation of application No. 16/586,980, filed on Sep. 28, 2019, now Pat. No. 11,033,880.

(Continued)

(51) Int. Cl.
*B01J 23/06* (2006.01)
*B01J 23/00* (2006.01)
(Continued)

(52) U.S. Cl.
CPC ............. *B01J 23/002* (2013.01); *B01J 23/06* (2013.01); *B01J 23/34* (2013.01); *B01J 23/6484* (2013.01);
(Continued)

(58) Field of Classification Search
CPC ............. B01J 2523/847; B01J 2523/56; B01J 23/002; B01J 23/10; B01J 23/30; B01J 23/6484; B01J 23/83
See application file for complete search history.

(56) References Cited

U.S. PATENT DOCUMENTS 2,279,198 A 4/1942 Huppke
3,948,808 A 4/1976 Box et al.
(Continued)

OTHER PUBLICATIONS

International Search Report and Written Opinion from International Application No. PCT/US2019/053711 dated Dec. 17, 2019.
(Continued)

*Primary Examiner* — Sharon Pregler
(74) *Attorney, Agent, or Firm* — Frank Rosenberg

(57) ABSTRACT

The invention relates to a catalyst composition suitable for the dehydrogenation of paraffins having 2-8 carbon atoms comprising zinc oxide and titanium dioxide, optionally further comprising oxides of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y), tungsten (W) and Zirconium (Zr) or mixtures thereof, wherein said catalyst composition is substantially free of chromium and platinum. The catalysts possess unique combinations of activity, selectivity, and stability. Methods for preparing improved dehydrogenation catalysts and a process for dehydrogenating paraffins having 2-8 carbon atoms, comprising contacting the mixed metal oxide catalyst with paraffins are also described. The catalyst may also be disposed on a porous support in an attrition-resistant form and used in a fluidized bed reactor.

17 Claims, 3 Drawing Sheets

Related U.S. Application Data

(60) Provisional application No. 62/849,721, filed on May 17, 2019, provisional application No. 62/739,140, filed on Sep. 28, 2018.

(51) Int. Cl.

| | | |
|---|---|---|
| *B01J 23/34* | (2006.01) | |
| *B01J 23/648* | (2006.01) | |
| *B01J 23/72* | (2006.01) | |
| *B01J 23/745* | (2006.01) | |
| *B01J 35/02* | (2006.01) | |
| *B01J 35/10* | (2006.01) | |
| *C07C 5/333* | (2006.01) | |
| *B01J 21/02* | (2006.01) | |
| *B01J 21/06* | (2006.01) | |
| *B01J 21/08* | (2006.01) | |

(52) U.S. Cl.
CPC ............ *B01J 23/72* (2013.01); *B01J 23/745* (2013.01); *B01J 35/023* (2013.01); *B01J 35/1014* (2013.01); *C07C 5/3332* (2013.01); *B01J 21/02* (2013.01); *B01J 21/063* (2013.01); *B01J 21/08* (2013.01)

(56) References Cited

U.S. PATENT DOCUMENTS

| | | | |
|---|---|---|---|
| 4,144,277 A | 3/1979 | Walker et al. | |
| 4,176,140 A | 11/1979 | Bertus et al. | |
| 4,327,238 A | 4/1982 | Eastman | |
| 4,389,337 A | 6/1983 | Eastman | |
| 4,524,144 A | 6/1985 | Aldag | |
| 5,220,091 A | 6/1993 | Brinkmeyer et al. | |
| 6,518,476 B1 | 2/2003 | Culp et al. | |
| 6,677,497 B2* | 1/2004 | Liu ...................... | C07C 5/3332 585/654 |
| 6,989,346 B2 | 1/2006 | Heineke et al. | |
| 7,087,802 B2 | 8/2006 | Schindler et al. | |
| 8,431,761 B2 | 4/2013 | Pan et al. | |
| 9,713,804 B2 | 7/2017 | Laha et al. | |
| 11,033,880 B2* | 6/2021 | Mukherjee ............. | B01J 37/036 |
| 2013/0165729 A1 | 6/2013 | Selvanathan et al. | |
| 2016/0074838 A1 | 3/2016 | Hock et al. | |
| 2019/0359543 A1 | 11/2019 | Jantharasuk et al. | |

OTHER PUBLICATIONS

International Search Report and Written Opinion from International Application No. PCT/US2019/053710 dated Dec. 17, 2019.
Schweitzer et al., "Propylene Hydrogenation and Propane Dehydrogenation by a Single-Site Zn2+ on Silica Catalyst", ACS Catalysis, 2014, 4, 1091-1098.
Sun et al., "Zn—Nb—O catalysts for propylene production via catalytic dehydrogenation of propane", Cat Comm vol. 50, 2014, pp. 73-77.
Harlin et al., "Alumina-Supported Vanadium Oxide in the Dehydrogenation of Butanes", Journal of Catalysis, 2000, vol. 195, p. 67-78.
Volpe et al., "Butane dehydrogenation on vanadium supported catalysts under oxygen free atmosphere", Applied Catalysis A vol. 272, 2004, p. 69-78.
Harlin et al., "Effect of Mg and Zr Modification on the Activity of VOx/Al2O3 Catalysts in the Dehydrogenation of Butanes", Journal of Catalysis, 2001, vol. 203, 242-252.
Harlin et al., "Activity of Molybdenum Oxide Catalyst in the Dehydrogenation of n-Butane", Journal of Catalysis, 1999, vol. 183, 300-313.
Xu et al., "Support effect in dehydrogenation of propane in the presence of CO2 over supported gallium oxide catalysts", Journal of Catalysis, 2006, vol. 239, 470-477.
Liu et al., "Ordered mesoporous carbon catalyst for dehydrogenation of propane to propylene", Chemical Communications, 2011, vol. 47, 8334-8336.
Chen et al., "Study in support effect of In2O3/MOx (M = Al, Si, Zr) catalysts for dehydrogenation of propane in the presence of CO2", Applied Catalysis A, 2011, vol. 407, 20-28.
Stobbe et al., "Potassium promotion of iron oxide dehydrogenation catalysts supported on magnesium oxide: 2. 1-Butene dehydrogenation activity", Journal of Catalysis, 1992, vol. 135, 548-562.
Shimada et al., "Dehydrogenation of isobutane to isobutene with iron-loaded activated carbon catalyst", Applied Catalysis A, 1998, vol. 168, 243-250.
Chen et al., "Dehydrogenation of Isobutane over Zinc Titanate Thin Film Catalysts", Journal of Catalysis, 1996, vol. 161, 730-741.
International Preliminary Report on Patentability from International Application No. PCT/US2019/053711, dated Mar. 23, 2021.
International Preliminary Report on Patentability from International Application No. PCT/US2019/053710, dated Mar. 23, 2021.

* cited by examiner

MIXED METAL OXIDE CATALYST USEFUL FOR PARAFFIN DEHYDROGENATION

RELATED APPLICATIONS

This application is a continuation of U.S. patent application Ser. No. 16/586,980 filed 28 Sep. 2019 and claims the priority benefit of U.S. Provisional Patent Application Ser. No. 62/739,140 filed 28 Sep. 2018 and U.S. Provisional Patent Application Ser. No. 62/849,721 filed 17 May 2019.

BACKGROUND

The US is currently undergoing a quiet revolution in fossil energy. Recent technological advances, specifically the confluence of horizontal drilling and hydraulic fracturing, have enabled vast gas reserves locked in shale formations to be cost effectively tapped for the first time. An estimated 2 quadrillion cubic feet of natural gas is held in these unconventional reserves in the US, enough to supply the nation's needs for many decades.

The ability to access these resources has led to a sudden decoupling of the traditional link between petroleum and natural gas prices. Domestic natural gas prices have fallen to historically low levels as a result of the introduction of 4.5 trillion cubic feet per year of shale gas, accounting for 20% of the nation's total gas supply.

The abundance of cheap propane, ethane, and methane from shale gas and stranded gas will facilitate cost-competitive paths in the production of commodity chemicals such as light olefins. In particular, the on-purpose production of propylene has grown as more steam crackers shift from naphtha feed to lighter shale condensates. This is especially true in the United States, where shale gas exploitation has grown exponentially, amplifying the issue of supply due to the strong growth in propylene demand compared with that of ethylene. Steam cracker units cannot fill this gap due to the low propylene/ethylene ratio. In this respect, other production routes could be profiled as an interesting alternative to overcome this issue.

The shift from naphtha toward light feeds that are derived from tight oil, for the production of ethylene in steam crackers, has impacted the global propylene and crude $C_4$ production capacity. Therefore, routes for the production of light olefins have received considerable interest. Catalytic dehydrogenation provides the possibility of high selectivity to a single olefin product—much higher than can be expected from steam crackers alone. The amount of propylene produced by dehydrogenation was 5 million tons in 2017 and is expected to increase.

Two patented industrial processes for the dehydrogenation of alkanes are currently in commercial use—namely, the Oleflex process which uses a Platinum-based catalyst and the Catofin process which uses a Chromium-based catalyst. Platinum is expensive and currently sells for $27,000/kg making platinum-based dehydrogenation processes very expensive. Chromium-based catalysts are comparatively cheaper. However, chromium is a known carcinogen. The object of the present invention is to provide an improved mixed-metal oxide catalyst for the dehydrogenation of paraffins which is essentially free of either Platinum or Chromium.

Compared to metallic platinum and chromium oxide, zinc oxide (ZnO) is an inexpensive and low-toxic alternative for dehydrogenation of propane. Zinc has been shown to activate propane through dissociative adsorption over zinc oxide species. For instance, U.S. Pat. No. 2,279,198 describes an active, stable and regenerable catalytic system consisting of zinc oxide along with other metal oxides and promoters for the dehydrogenation of alkanes and other organic compounds. Isobutane conversion as high as 26.4% has been reported at 510° C. Successively precipitated ZnO over zirconium oxide was shown to be active and stable for the dehydrogenation reaction while addition of small amounts of $Li_2O$ and CaO were shown to further improve the catalyst activity and stability.

Numerous other Zn-based catalysts have been explored for dehydrogenation of hydrocarbons. For example, it is reported that when Zn is introduced into acidic zeolites like H-ZSM5, the reaction rate for dehydrogenation of paraffins increases[2-13]. The $Zn^{2+}$ species are reported to reside in the cation exchange sites of the zeolite and have a tetrahedral orientation. The main products are aromatic compounds and the selectivity to olefins is usually low (<40%). While the role of Zn in these reactions is greatly debated, it is believed that Zn carries out the two-fold function of promoting the dehydrogenation of the hydrocarbon as well as depleting the surface hydrogen pool by the catalytic recombinative desorption of H-atoms and $H_2$[14]. Zinc has also been used as a promoter for alkane dehydrogenation catalysts[15-20]. For example, studies in literature have shown that the addition of Zn to Pt or Cr containing catalysts resulted in increasing the alkene selectivity during alkane dehydrogenation. It is believed that zinc modifies the geometric and electronic properties of the metallic phase of Pt and studies showed that the addition of zinc to Pt—$Al_2O_3$, PtSn—$Al_2O_3$,[15] and PtSn—$MgAl_2O_4$ formulations significantly improved their overall performance for propane dehydrogenation[17]. Zinc is known to alloy with platinum and the formation of the alloy is believed to increase the electronic density on the metallic Pt which weakens the alkene adsorption[15] resulting in reduced coke formation and lower associated by-product gases such as methane and ethane.

Zinc was also shown to be effective in increasing the activity of hematite towards ethylbenzene dehydrogenation[21]. The authors claimed that while zinc oxide by itself was inactive for the reaction, it increased the activity of hematite towards the dehydrogenation by stabilizing the $Fe^{3+}$ species.

Zinc based catalysts have been shown to be active in the oxidative dehydrogenation of hydrocarbons. While it was known that simple iron oxide, $\alpha$-$Fe_2O_3$ catalyzes a rather selective production of butadiene via the oxidative dehydrogenation of butenes and in some cases n-butane, Rennard and Kehl showed that addition of zinc oxide to iron oxide leads to the formation of $ZnFe_2O_4$ which further increases the selectivity to butadiene under identical conditions[22]. For example, the selectivities for butadiene on $Fe_2O_3$ were 83% at 325° C. and 43% at 375° C., while on $ZnFe_2O_4$ they were 89% at 325° C. and 88% at 375° C. Comparison of these results with those on iron oxide suggests that zinc ferrite is a more selective oxidation catalyst because it has a higher density of selective oxidation sites and a lower density of combustion sites, and because its combustion sites are less active than those on iron oxide[22-24]. Numerous methods of synthesis with and without the presence of promoters have been described in literature (U.S. Pat. Nos. 3,743,683, 3,951,869). For example, it is reported that when a zinc ferrite catalyst doped with chromium or aluminum was used, catalytic activity towards dehydrogenation was increased[25].

Zinc has been used as a support for the dehydrogenation of lower alkanes. Zinc aluminate has been used as a catalyst support due to its low specific surface area and high hydrothermal stability 26-28. U.S. Pat. Nos. 5,344,805; 5,430,220;

and EP 0557982A2 describe a process for dehydrogenating at least one alkane comprising 2 to 8 carbon atoms to an alkene in the presence of steam and a catalyst composition comprising zinc aluminate and platinum. The addition of zinc oxide to alumina for a Pt based catalyst was shown to increase the rate of dehydrogenation as well as the selectivity of alkene as a result of the suppression of the decomposition reaction and coke formation[29]. However, zinc aluminates by themselves are inactive as dehydrogenation catalysts. They require an additional metal like platinum as part of the catalyst composition to be effective.

Pt and Cr free catalysts have been synthesized via a coprecipitation method using nitrates of various metals and were shown to be active and selective for the dehydrogenation of isobutane to isobutene (U.S. Pat. No. 9,713,804B2, WO2013091822A1). The most active, selective and stable composition consisted of mixed Zn, Mn and Al oxides. Numerous promoters, selected from alkali metals (K, Cs), non-metals (Si) and transition metals (Fe, Cr, Cu, Zr, Ce etc.) were used to promote these catalysts with varying degrees of success. These catalysts showed high activity (upto 56% conversion of isobutane) and high selectivity (upto 96%) to isobutene at 550° C. and a space velocity of 0.6 hr-1. These catalysts also showed reasonable stability with just a moderate drop in activity for up to 500 reaction-regeneration cycles. However, no data was provided for the application of this catalyst to other hydrocarbons like ethane and propane. Zinc titanate is reported to be active in the dehydrogenation of alkanes. Zinc titanate was first reported to be active for the dehydrogenation of isobutane by Phillips Petroleum resulting in a modest isobutene yield. Later, it was also applied for the dehydrogenation of a number of paraffins, olefins, cycloaliphatics and alkyl aromatic compounds having from 2 to 12 carbon atoms per molecule as described in U.S. Pat. Nos. 4,368,344A, 4,389,337A, 4,524,144A, 4,144,277A, 4,394,297A, 4,218,346A.

U.S. Pat. Nos. 4,228,040A, 4,389,337, 4,463,213, 4,176,140 and 4,327,238 show that various promoters, either transition metals, alkali metals or alkaline earth metals can be used with the zinc titanate of U.S. Pat. No. 4,144,277 to improve the yield of unsaturated compounds. The catalyst was usually prepared by intimately mixing suitable proportions of zinc oxide and titanium dioxide wherein the atomic ratio of zinc to titanium was usually close to 2:1 and calcining the resulting mixture in air at a temperature in the range of 675° to 975° C. The catalysts were also prepared by coprecipitation of a mixture of aqueous solutions of a zinc compound and a titanium compound. The aqueous solutions were mixed together and the hydroxides were precipitated by the addition of ammonium hydroxide. The precipitate was then washed, dried and calcined. Promoters were either added during the coprecipitation with zinc and titanium compounds or the zinc and titanium were first coprecipitated and the coprecipitate was then impregnated with a suitable amount of the promoter. These patents report that the most active zinc orthotitanate catalyst was obtained when the titania particle size was small or when the catalysts were prepared by coprecipitation.

High yields of the unsaturated compounds were reported. Ethylene yield of 33% from ethane at 666° C. (U.S. Pat. No. 4,389,337), propylene yield of 67.75% at 621° C. (U.S. Pat. No. 4,228,040) and isobutene yield of 54% at 625° C. (U.S. Pat. No. 4,463,213) are reported to list a few. Usually, the reaction time was 3 minutes followed by a nitrogen purge for 3 minutes and then regeneration in air for 6 minutes. It is mentioned that the catalysts are subjected to numerous reaction-regeneration cycles. However, since no stability data is presented it is not clear whether the catalyst performance changes over the course of time with successive reaction-regeneration cycles. It should also be noted that the dehydrogenation tests were carried out in the presence of nitrogen as a diluent.

Lysova et al. studied the effect of the chemical composition of the $ZnO—TiO_2$ catalytic system on its phase composition and catalytic properties in the oxidative and non-oxidative dehydrogenation of isobutane[30]. It was found that samples with an atomic ratio of zinc to titanium≥2 exhibited the highest selectivity with high specific activity. It was reported that $ZnO—TiO_2$ system was active and selective in ODH of isobutane at 570° C., the maximum yield of isobutene being 54%.

Chen et al. prepared thin films (80-100 nm) of zinc titanate with Zn/Ti ratios between 0.5 and 2.7 on 200 Si(100) wafers via the metalloorganic decomposition (MOD) technique and investigated them for alkane dehydrogenation reactions[31]. Catalytic testing of these films for isobutane dehydrogenation showed a clear correlation between the structure and the catalytic performance which depended on the film stoichiometry. Zinc titanate phases, with a Zn/Ti ratio close to 2 had a cubic crystal structure and were found to be active for dehydrogenation while the other phases were not. The isobutane conversion was 2% at 823 K and 8 mol % at 923 K, with a selectivity of 90% to isobutene.

$Zn/SiO_2$—Schweitzer et al. tested a $Zn/SiO_2$ catalyst for the dehydrogenation of propane[32]. The reaction was run under differential conditions (target conversion of less than 10%). Propylene selectivity was reported to be >95% at 550 C and the catalyst lost only 50% of its activity in 12 hours. In this catalyst, the $Zn^{2+}$ center is coordinated with three O centers of the SiO2 surface and is believed to be the active species. It was shown through various computational and characterization methods that the active site catalyzes the heterolytic cleavage of the C—H bonds of propane and the undesired C—C cleavage reactions are shown to be kinetically less favorable resulting in a higher propylene selectivity. However, the dehydrogenation reaction was run with an extremely dilute 3% propane in Argon reaction mixture. Additionally, while it was mentioned that conversion reached 20% at 550° C., no time on stream data is provided for high conversions.

Sun et al. report that Zn—Nb—O oxides are active and selective in the catalytic dehydrogenation of propane to propylene[33]. A propylene yield of 28.1 wt. % with selectivity of 84% were observed over the catalyst which was calcined at 600° C. and had a molar ratio of $ZnO/Nb_2O_5$=3. $ZnNb_2O_6$ was suggested to be the active site for the dehydrogenation reaction. Temporary, reversible deactivation was observed which was attributed to the formation of coke while the loss of ZnO species leading to the formation of $Zn_3Nb_2O_8$ phase was suggested to be the reason for the irreversible deactivation of the catalyst.

U.S. Pat. No. 7,087,802, US Published Patent Application No. 2016/0074838 and U.S. Pat. No. 6,518,476 describe catalyst systems for the oxidative and/or non-oxidative dehydrogenation of light alkanes where the catalyst consists of a support and an active component. The support is generally a heat-resistant oxide and could be selected from zirconium dioxide, zinc oxide, aluminum oxide, silicon dioxide, titanium dioxide, magnesium oxide, lanthanum oxide, cerium oxide and mixtures thereof. The active component could be a precious metal like Pt or Pd or can be from the other transition, alkali or alkaline earth metal or a mixture of the above components. It was also suggested that the dehydrogenation catalyst described in these patents can be used in the form of a fixed bed in the reactor or in the form of a fluidized bed with an appropriate shape.

Despite these and other efforts, there remains a need in the industry to develop cost-effective, environmentally friendly dehydrogenation catalysts that are commercially viable.

FOOTNOTED CITATIONS

2. Mole, T., Anderson, J. R., and Creer, G., Appl. Catal. 17, 141 (1985).
3. Shibata, M., Kitagawa, H., Sendoda, Y., and Ono, Y., in "Proceedings of 7th International Zeolite Conference," p. 717. Elsevier, Tokyo, 1986.
4. Scurrell, M. S., Appl. Catal. 41, 89 (1988).
5. Ono, Y., and Kanae, K., J. Chem. Soc.-Faraday Trans. 87, 669 (1991).
6. Roessner, F., Hagen, A., Mroczek, U., Karge, H. G., and Steinberg, K. H., in "Proceedings of the 10th International Congress on Catalysis" (L. Guczi, F. Solymosi, and P. Tetenyi, Eds.), p. 1707. Elsevier, Budapest, 1992.
7. Iglesia, E., and Baumgartner, J. E., in "Abstracts 206th American Chemical Society Meeting," Chicago, Ill., 1993, p. 746.
8. Dufresne, L. A., and le van Mao, R., Catal. Lett. 25, 371 (1994).
31. Hagen, A., Roessner, F., and Reschetilowski, W., Chem. Eng. Technol. 18, 414 (1995).
9. Biscardi, J. A., and Iglesia, E., Catal. Today 31, 207 (1996).
10. Berndt, H., Lietz, G., Lucke, B., and Volter, J., Appl. Catal. 146, 351 (1996).
11. Berndt, H., Lietz, G., and Volter, J., Appl. Catal. 146, 365 (1996).
12. Kwak, B. S., and Sachtler, W. M. H., Korean J. Chem. Eng. 13, 356 (1996).
13. Viswanadham, N., Pradhan, A. R., Ray, N., Vishnoi, S. C., Shanker, U., and Prasada Rao, T. S. R., Appl. Catal. 137, 225 (1996).
14. Joseph A. Biscardi, Enrique Iglesia, Journal of Catalysis, (1999) 182, 117-128.
15. Yu C L, Xu H Y, Ge Q J, Li W Z. J Mol. Catal A Chem. 2007; 266(1-2):80-87.
16. Zhang Y W, Zhou Y W, Shi J J, Sheng X L, Duan Y Z, Zhou S J, Zhang Z W. Fuel Process Technol. 2012; 96:220-227.
17. Wang Y J, Wang Y M, Wang S R, Guo X Z, Zhang S M, Huang W P, Wu S H. Catal Lett. 2009; 132(3-4):472-479.
18. Silvestre-Albero J, Serrano-Ruiz J C, Sepulveda-Escribano A, Rodriguez-Reinoso F. Appl Catal A Gen. 2005; 292:244-251.
19. Bosch P, Valenzuela M A, Zapata B, Acosta D, Aguilarrios G, Maldonado C, Schifter I. J Mol Catal. 1994; 93(1):67-78.
20. Yu, Z.; Sawada, J. A.; An, W.; Kuznicki, S. M. AIChE J. 2015, 61, 4367-4376.
21. Hugo Ernane Leite Bomfim, Alcineia Conceição Oliveira and Maria do Carmo Rangel; React. Kinet. Catal. Lett. (2003), 80, 2, 359.
22. Rennard, R.; Kehl, W. J. Catal. (1971), 21, 282.
23. H. Kung,* B. Kundalkar, M. C. Kung, and W. H. Cheng J. Phys. Chem., (1980) Vol. 84, No. 4, 382-388
24. F.-Y. Qiu, L.-T. Weng, E. Sham, P. Ruiz, B. Delmon, (1989) Appl. Catal., 51, 235.
25. J. A. Toledo, P. Bosch, M. A. Valenzuela, A. Montoya, N. Nava; (1997) J. Mol. Catal. A, 125, 3.
26. A. Kiennemann, H. Idriss, J. P. Hindermann, J. C. Lavalley, A. Vallet, P. Chaumette and P. Courty, Appl. Catal. 59 (1990) 165.
27. G. P. Chernyuk, L. I. Chelyadin and Y. S. Mazurenko, Neftekhimiya 16 (1976) 683.
28. M. E. Olbrich and J. H. Kolts, AICHE Spring Nat. Meet., New Orleans, Apr. 6-10, 1986.
29. Hideki SATOH, Hiroyuki TAGUCHI, Hiroshi MIURA; J. Japan Petroleum Institute, 1995, 38, 1, 34-39.
30. N. N. Lysova, D. N. Tmenov and P. Luk'yanenko, Russ. Zh. Prikl. Khim., 65 (1992), 1848; J. Appl. Chem. (1993) 1500 (Engl. translation).
31. Z. X. Chen, A. Derking, W. Koot, and M. P. van Dijk; JOURNAL OF CATALYSIS (1996) 161, 730-741.
32. Neil M. Schweitzer, Bo Hu, Ujjal Das, Hacksung Kim, Jeffrey Greeley, Larry A. Curtiss, Peter C. Stair, Jeffrey T. Miller, and Adam S. Hock; ACS Catal. (2014), 4, 1091-1098.
33. Ya-nan Sun, Chuancheng Gao, Lei Tao, Guowei Wang, Dongmin Han, Chunyi Li, Honghong Shan; Catalysis Communications; 50 (2014) 73-77.

SUMMARY OF THE INVENTION

In a first aspect, the invention provides a mixed metal oxide catalyst suitable for the dehydrogenation of paraffins having 2-8 carbon atoms with a catalyst composition of the general formula (AC) (CS) (ST) wherein
a) AC represents oxides of Transition Metals selected from the group of copper (Cu), iron (Fe), manganese (Mn), niobium (Nb) and zinc (Zn) or mixtures thereof,
b) CS represents oxides of aluminum (Al), silicon (Si), titanium (Ti) and zirconium (Zr) or mixtures thereof,
c) ST represents oxides of Rare Earth metals selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), and yttrium (Y) or mixtures thereof, and
characterizable by an Activity Parameter >1500, Selectivity Parameter <0.2 and a stability parameter <0.005 using a test where the mixed metal oxide catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream of propane at a temperature of 625° C., atmospheric pressure and a feed rate of 1 $hr^{-1}$ or 2 $hr^{-1}$ weight hourly space velocity.

In a related aspect, the invention provides a mixed-metal oxide catalyst suitable for the dehydrogenation of paraffins having 2-8 carbon atoms comprising oxides of Transition Metals selected from the group of copper (Cu), iron (Fe), manganese (Mn), niobium (Nb) and zinc (Zn) as the active catalytic species wherein the active species makes up 0.1 to 20 wt % of the total weight of the catalyst, preferably 0.1 to 7.5 wt %, oxides of aluminum (Al), silicon (Si), titanium (Ti) and zirconium (Zr) or mixtures thereof as the catalyst support wherein the catalyst support makes up 10 to 90 wt % of the total weight of the catalyst, preferably 50 to 80 wt % and oxides of Rare Earth metals as catalyst stabilizers selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), and yttrium (Y)

wherein the catalyst stabilizer makes up 0.1 to 20 wt % of the total weight of the catalyst, preferably 1 to 10 wt % and characterizable by
  a) Activity Parameter>1500,
  b) Selectivity Parameter <0.2, and
  c) Stability parameter <0.005
  measured using a test where the metal oxide catalyst is loaded in a fixed-bed reactor such that the $50>d_T/d_P>10$ (diameter of tube to diameter of catalyst particles) and $200>L/d_P>50$ (length of catalyst bed to diameter of catalyst particles) and $2>d_P>0.5$ mm exposed to a feed stream comprising of propane at a temperature of 625° C., atmospheric pressure and a feed rate of 1 $hr^{-1}$ weight hourly space velocity.

In a further aspect, the invention provides mixed metal oxide catalyst suitable for the dehydrogenation of paraffins having 2-8 carbon atoms with a catalyst composition of the general formula (AC) (CS) (ST) wherein
  a) AC represents oxides of Transition Metals selected from the group of copper (Cu), iron (Fe), manganese (Mn), niobium (Nb) and zinc (Zn) or mixtures thereof,
  b) CS represents oxides of aluminum (Al), silicon (Si), and titanium (Ti) or mixtures thereof,
  c) ST represents oxides of Rare Earth metals selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y), tungsten (W), zirconium (Zr), or mixtures thereof, and
  characterizable by a Activity Parameter >1500, Selectivity Parameter <0.2 and a stability parameter <0.005 using a test where the mixed metal oxide catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream of propane at a temperature of 625° C., atmospheric pressure and a feed rate of 1 $hr^{-1}$ or 2 $hr^{-1}$ weight hourly space velocity.

In another aspect, the invention provides mixed metal oxide catalyst comprising a catalyst composition of the general formula (AC) (CS) (ST) (MS) wherein
  a) AC (Active Catalyst) represents oxides of Transition Metals selected from the group of copper (Cu), iron (Fe), manganese (Mn), niobium (Nb) and zinc (Zn) or mixtures thereof,
  b) CS (Catalyst Support) represents oxides of aluminum (Al), silicon (Si), and titanium (Ti) or mixtures thereof,
  c) ST (Support Stabilizer) represents oxides of metals selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y) Tungsten (W) and zirconium (Zr) or mixtures thereof,
  d) MS (Mechanical Stabilizer) represents porous spheres selected from the group of alumina, silica, titania, zirconia, kaolin, meta-kaolin, bentonite, attapulgite, or mixtures thereof;
  and characterizable by a Activity Parameter >1500, Selectivity Parameter <0.5 and a stability parameter <0.005 using a test where the mixed metal oxide catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream of propane at a temperature of 625° C., atmospheric pressure and a feed rate of 2 $hr^{-1}$ weight hourly space velocity.

In a preferred embodiment, the MS (mechanical stabilizer) species makes up 20 to 85 wt % of the total weight of the catalyst.

In order to characterize a catalyst, it is loaded into a fixed bed. Fine catalyst powders can be characterized by the same measurement by pelletizing the fine powder into a size suitable for fixed bed testing.

In a further aspect, the invention provides catalyst composition comprising zinc oxide with optional modifiers selected from the group of Copper, Manganese, and Niobium and a stabilized titania support, comprising: the stabilized titania support stabilized with a stabilizing element comprising zirconium, tungsten, or a rare earth element or combinations thereof; and Zn; wherein the catalyst composition from 10 to 95 wt % titania, 0.1 to 25 wt % of the stabilizing element(s), 0 to 3 wt % of the modifiers; and 0.1 to 10 wt % Zn; and characterizable by an Activity Parameter >1500, Selectivity Parameter <0.2 and a stability parameter <0.005 using a test where the mixed metal oxide catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream of propane at a temperature of 625° C., atmospheric pressure and a feed rate of 1 $hr^{-1}$ (or 2 $hr^{-1}$) weight hourly space velocity.

Since the catalysts cannot be completely distinguished from the prior art based solely on their elemental composition, the measurement described above is needed for a unique characterization of the catalyst. In various embodiments, the catalyst may be further characterized by any of the compositions or physical characteristics described herein.

In various embodiments, any of the catalysts can be further characterized by one or any combination of the following: comprising less than 100 ppm or less than 50 ppm by weight of either platinum (Pt) or chromium (Cr); wherein the Brunauer-Emmet-Teller (BET) surface area >30 $m^2/g$; wherein the number average particle size of the mixed-metal oxide catalyst is in the range of 30-3000 microns; wherein the Air Jet Index is less than 10 and most preferably less than 5; wherein the active catalyst species makes up 0.1 to 10 wt % of the total weight of the catalyst; wherein the active catalyst species makes up 0.1 to 7.5 wt % of the total weight of the catalyst; wherein the CS (catalyst support) makes up 10 to 95 wt % of the total weight of the catalyst; wherein the catalyst support makes up 20 to 90 wt % of the total weight of the catalyst; wherein the catalyst support makes up 50 to 85 wt % of the total weight of the catalyst; wherein the ST (catalyst stabilizer) makes up 0.1 to 25 wt % of the total weight of the catalyst; wherein the catalyst stabilizer makes up 1 to 15 wt % of the total weight of the catalyst; wherein the catalyst stabilizer makes up 1 to 10 wt % of the total weight of the catalyst; wherein the catalyst support comprises a mesoporous bead and wherein the number average particle size of the mesoporous bead is in the range of 30-3000 micrometers.

In another aspect, the invention provides method of synthesizing a mixed-metal oxide catalyst suitable for the dehydrogenation of paraffins by first contacting the catalyst support with a solution comprising a salt solution of a rare earth metal, calcining the catalyst support by heating said catalyst support impregnated with rare earth metals to produce a stabilized catalyst support, contacting the stabilized catalyst support with a salt solution of a transition metal and finally calcining the catalyst intermediate to produce the final form of catalyst wherein the particle diameter of the final catalyst is 30-3000 microns.

In another aspect, the invention provides a method of synthesizing the catalyst support using a sol gel procedure where the organic alkoxide of the support or mixtures are first dissolved in an organic solvent, the solution is hydrolyzed using either a mineral acid or base. Finally, the resultant sol-gel mixture/s is dried and calcined to produce the catalyst support. The catalyst support is then contacted with a solution comprising a salt solution of a rare earth metal, calcining the catalyst support by heating said catalyst support impregnated with rare earth metals to produce a stabilized catalyst support. The stabilized catalyst support is then impregnated with a salt solution of a mixture of transition metals and finally calcining the catalyst intermediate to produce the final form of catalyst wherein the particle diameter of the final catalyst is 30-3000 microns (μm).

In another aspect, the invention provides a method of synthesizing the catalyst support using a co-precipitating procedure where the salts of the support or mixtures are first dissolved in water, co-precipitating the salts from the solution using a precipitating agent. Finally, the resultant precipitate is dried and calcined to produce the catalyst support. The catalyst support is then contacted with a solution comprising a salt solution of a rare earth metal, calcining the catalyst support by heating said catalyst support impregnated with rare earth metals to produce a stabilized catalyst support. The stabilized catalyst support is then impregnated with a salt solution of a mixture of transition metals and finally calcining the catalyst intermediate to produce the final form of catalyst wherein the number average particle size of the final catalyst is 30-3000 microns (μm).

In another embodiment, the catalyst support is first grafted onto a mesoporous bead where the pore dimeter of the mesoporous bead is 3-25 nanometers. The objective is to provide the catalyst with sufficient mechanical strength required to operate in fluidized bed reactor. The grafting of the catalyst support is accomplished by first dissolving the organic alkoxide of the support or mixtures in an organic solvent, impregnating the pores of the mesoporous beads with the organic alkoxide solution, drying and calcining the mesoporous beads to produce the grafted catalyst support. The catalyst support or the final catalyst is calcined preferably at 550-650° C. for 2-24 hrs in air. The grafted catalyst support is impregnated with a salt solution of a mixture of transition metals and finally calcining the catalyst intermediate to produce the final form of catalyst wherein the particle size of the final catalyst is 30-3000 microns.

In another embodiment, the grafting of the catalyst support is accomplished by first dissolving salts of the support or mixtures in water, impregnating the pores of the mesoporous beads with the salt solution, drying and calcining the mesoporous beads to produce the grafted catalyst support. The catalyst support or the final catalyst is calcined preferably at 550-650° C. for 2-24 hrs in air. The grafted catalyst support is impregnated with a salt solution of a mixture of transition metals and finally calcining the catalyst intermediate to produce the final form of catalyst wherein the particle size of the final catalyst is 30-3000 microns.

In another aspect, the invention provides a method for preparing a catalyst comprising the steps of: a) dissolving salts of active material, catalyst support and support stabilizer in a solvent; b) coprecipitating the salts using a precipitating agent; and c) drying and calcining the resultant precipitate to produce the mixed metal oxide catalyst.

In another aspect, the invention provides a method for preparing a catalyst comprising the steps of:
a) providing a salt solution comprising salts of Al, Si, Ti, or Zr or mixtures thereof dissolved in water;
b) impregnating mesoporous beads with the salt solution;
c) drying and calcining the mesoporous beads to produce the grafted catalyst support;
d) contacting the catalyst support with a solution comprising a salt of a rare earth metal or mixtures thereof;
followed by addition of rare-earth and transition metals comprising the steps of
e) calcining said catalyst support by heating said catalyst support impregnated with rare earth metals to produce a stabilized catalyst support;
f) contacting the stabilized catalyst support with a solution comprising a salt of a transition metal or mixtures thereof to make a catalyst intermediate; wherein the transition metal is selected from the group of consisting of: copper (Cu), iron (Fe), manganese (Mn), niobium (Nb) and zinc (Zn) or mixtures thereof; and
g) calcining the catalyst intermediate to produce the mixed metal oxide catalyst.

In another aspect, the invention provides a method for preparing a catalyst comprising the steps of:
a) dissolving organic alkoxides of catalyst support and support stabilizer in an organic solvent,
b) contacting the organic alkoxide solution or mixtures thereof with porous spheres,
c) drying and calcining the porous spheres to produce the grafted catalyst support,
d) contacting the grafted catalyst support with a solution comprising a salt of active catalyst metal or mixtures thereof,
e) calcining the catalyst intermediate to produce the mixed metal oxide catalyst.

In another aspect, the invention provides a method for preparing a catalyst comprising the steps of:
a) providing a salt solution comprising salts of catalyst support and support stabilizer dissolved in a solvent;
b) impregnating porous spheres with the salt solution;
c) drying and calcining the porous spheres to produce the grafted catalyst support;
d) contacting the grafted catalyst support with a solution comprising a salt of a transition metal or mixtures thereof to make a catalyst intermediate; wherein the transition metal is selected from the group of consisting of: copper (Cu), iron (Fe), manganese (Mn), niobium (Nb) and zinc (Zn) or mixtures thereof; and
e) calcining the catalyst intermediate to produce the mixed metal oxide catalyst.

In another aspect, the invention provides a method for preparing a catalyst comprising the steps of:
a) providing a salt solution comprising salts of active catalyst, catalyst support, and support stabilizer dissolved in a solvent;
b) impregnating porous spheres with the salt solution; and
c) drying and calcining the porous spheres to produce the mixed metal oxide catalyst.

In another aspect, the invention provides a method for preparing a catalyst composition comprising the steps of:
a) optionally, contacting the catalyst support with a solution comprising a salt of a rare earth metal or mixtures thereof to produce an impregnated catalyst support;

b) optionally, calcining said catalyst support by heating said catalyst support impregnated with the rare earth metals to produce a stabilized catalyst support;

c) contacting the stabilized catalyst support with a solution comprising a salt of the transition metal or mixtures thereof, d) calcining the catalyst intermediate to produce the mixed metal oxide catalyst.

In some preferred embodiments, the catalyst support is synthesized using a sol gel procedure comprising the steps of a) dissolving organic alkoxides of catalyst support and support stabilizer in an organic solvent; b) hydrolyzing the organic alkoxide solution, preferably in the presence of an acid or base catalyst, to produce a gel; and c) drying and calcining the resultant gel to produce the catalyst support.

In some embodiments, the catalyst support is synthesized using inorganic salts comprising the steps of: a) dissolving salts of catalyst support and support stabilizer in a solvent; b) coprecipitating the salts using a precipitating agent; and c) drying and calcining the resultant precipitate to produce the catalyst support.

In another aspect, the invention provides a method for preparing a catalyst comprising the steps of:

a) dissolving the organic alkoxide of the support or mixtures thereof in an organic solvent b) contacting the organic alkoxide solution or mixtures thereof with mesoporous beads c) drying and calcining the mesoporous beads to produce the grafted catalyst support d) contacting the catalyst support with a solution comprising a salt of a rare earth metal or mixtures thereof; followed by addition of rare-earth and transition metals comprising the steps of e) calcining said catalyst support by heating said catalyst support impregnated with rare earth metals to produce a stabilized catalyst support;

f) contacting the stabilized catalyst support with a solution comprising a salt of a transition metal or mixtures thereof; and g) calcining the catalyst intermediate to produce the mixed metal oxide catalyst.

In another aspect, the invention provides a method for preparing a catalyst comprising the steps of: a) providing a salt solution comprising salts of Al, Si, Ti, or Zr or mixtures thereof dissolved in water; b) impregnating mesoporous beads with the salt solution; c) drying and calcining the mesoporous beads to produce the grafted catalyst support; d) contacting the catalyst support with a solution comprising a salt of a rare earth metal or mixtures thereof; followed by addition of rare-earth and transition metals comprising the steps of: e) calcining said catalyst support by heating said catalyst support impregnated with rare earth metals to produce a stabilized catalyst support; f) contacting the stabilized catalyst support with a solution comprising a salt of a transition metal or mixtures thereof to make a catalyst intermediate; wherein the transition metal is selected from the group of consisting of: copper (Cu), iron (Fe), manganese (Mn), niobium (Nb) and zinc (Zn) or mixtures thereof; and g) calcining the catalyst intermediate to produce the mixed metal oxide catalyst.

In any of the methods of making the catalyst support or the mixed metal oxide catalyst, in some embodiments, the support or catalyst be calcined at 500-1,100° C., preferably at 550-800° C. and most preferably at 550-650° C. for 2-6 hrs in an oxygen containing atmosphere, preferably air. In some embodiments, the volume average pore diameter of the mesoporous bead is in the range of 3-500 nm or 3-25 nm.

The invention also includes processes of dehydrogenating a paraffin (preferably propane or isobutane), comprising contacting the paraffin with any of catalysts described herein in a reaction chamber under conditions sufficient to dehydrogenate the paraffin and resulting in an olefin. The sufficient conditions are conventional conditions for dehydrogenation or identified with no more than routine experimentation.

In a further aspect, the invention provides a process for continuous dehydrogenating of paraffins having 2-8 carbon atoms, preferably propane or isobutane, comprising: contacting said paraffins with any of the catalyst compositions described herein at a reaction temperature of 500-800° C., a space velocity of 0.1-5 $hr^{-1}$ or 0.1-1 $hr^{-1}$ and a pressure of 0.01-0.2 MPa for a reaction period in the range of 0.05 seconds to 10 minutes; regenerating the said catalyst with an oxygen-containing gas wherein said catalyst regeneration is performed at a reaction temperature of 500-800° C., a pressure of 0.01-0.2 MPa and a regeneration period ranging from 0.05 seconds to 10 minutes. In some preferred embodiments, the contacting step is carried out in a fluidized bed reactor or a fixed-bed swing reactor.

Another aspect of the invention provides a continuous method for dehydrogenating paraffins having 2-8 carbon atoms wherein the process is performed at a reaction temperature of 500-800° C., a space velocity of 0.1-1 $h^{-1}$ and a pressure of 0.01-0.2 MPa. The fluidized bed version of the method is shown in FIG. 1. In this method, the paraffin feedstock 1 is contacted with the catalyst under dehydrogenation conditions for a reaction period in the range of about 0.05 second to 10 minutes in Reactor/Riser A. Following the reaction period, the Reactor outlet stream 2 containing catalyst and product gas flows to the Cyclone/Disengager B in which the catalyst is separated from the Product Stream 3. The Separated Catalyst stream 4 is thereafter regenerated in Regenerator C by contacting said catalyst with Combustion Air 5. The catalyst regeneration is performed at a temperature of 500-800° C., a pressure of 0.01-0.2 MPa and a regeneration period ranging from about 0.05 seconds to 10 minutes and producing Flue Gas stream 6 and Regenerated Catalyst stream 7, which is routed again to the Reactor/Riser A. The process can be carried out using a Reactor/Riser A configured as a fluidized bed reactor or as a fixed-bed swing reactor.

In some preferred embodiments, the invention provides advantages such as: the product of the catalyst activity and catalyst selectivity exceeding 0.1 ton of product per hour per ton of catalyst; and the overall catalyst consumption does not exceed 1 kg of catalyst per ton of product. None of the prior art catalysts listed in the prior art meet these three characteristics simultaneously.

GLOSSARY

Figure 1:
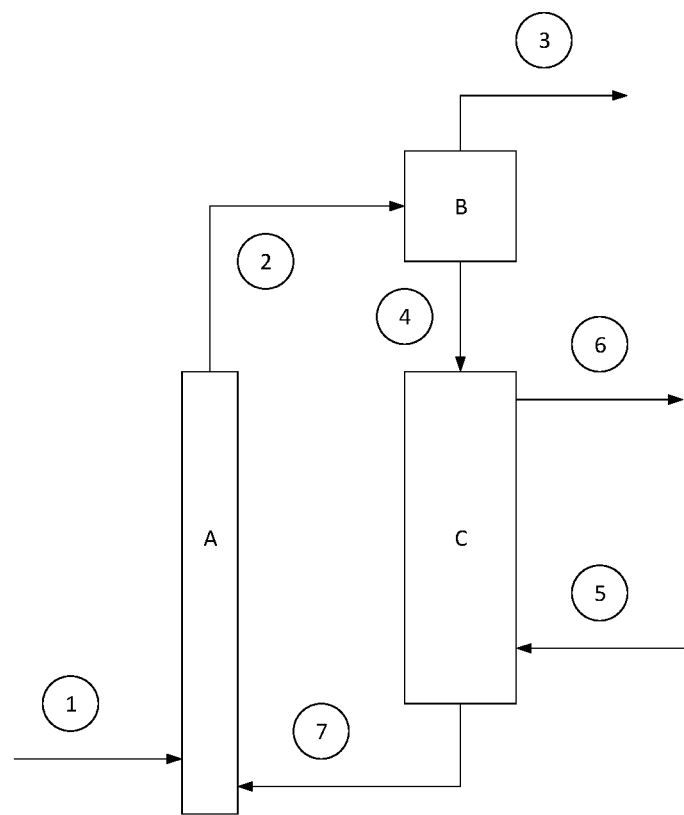
FIG. 1 schematically illustrates a continuous method for dehydrogenating paraffins in a fluidized bed reactor.

Arrhenius Activation Energy (E): The Arrhenius equation gives the quantitative basis of the relationship between the activation energy and the rate at which a reaction proceeds.

Arrhenius activation energy term from the Arrhenius equation is as an experimentally determined parameter that indicates the sensitivity of the reaction rate to temperature. From the equation, the activation energy can be found through the relation $$k=k_0 e^{-E/RT}$$

Where k is the rate constant of a reaction at temperature T, $k_0$ is pre-exponential factor, E is activation energy for the reaction, R the universal gas constant, T the reaction temperature (in Kelvin). k is calculated from conversion (x) and residence time ($\tau$) as follows $$k=-\ln(1-x)/\tau$$

Activity Parameter—The catalyst activity is quantified by the activity parameter which is the pre-exponential factor in the Arrhenius equation $k_0$ for the dehydrogenation reaction, an empirical relationship between temperature and rate coefficient using a value of 81.7 kJ/mole for E the Activation Energy for the dehydrogenation reaction using for Titania based catalyst.

Selectivity Parameter—Since selectivity of propylene varies with propane conversion, a method is required to compare selectivity obtained by different catalysts under various conversions. Selectivity parameter is calculated from the ratio of the rate constant of the propylene cracking reaction ($k_c$) measured in the absence of any diluent such as nitrogen, steam, helium or hydrogen to the rate constant of the propane dehydrogenation reaction ($k_d$) and remains constant irrespective of the propane conversion. A catalyst producing propylene with a high selectivity will have a selectivity parameter <0.2.

The selectivity parameter ($=k_C/k_D$) is calculated from propane conversion (x) and propylene yield (y) by solving the equations shown below:

$$k_D=-\ln(1-x)/\tau$$

$$y=[k_D/(k_C-k_D)][e^{(-kD\tau)}-e^{(kC\tau)}]$$

Stability Parameter—The loss of catalyst activity with time is quantified by the stability parameter which measures the rate of change of catalyst activity with time. A catalyst with high stability will have a low stability parameter value <0.005.

$$\text{Stability Parameter}=|(k_{Dt}-k_{D0})|/(k_{D0}*t)$$

Where $k_{Dt}$ is the rate constant of dehydrogenation of propane at time=t, $k_{D0}$ is the rate constant of dehydrogenation of propane at time=0 and t is the time on stream For instance, at a reaction temperature of T=625° C. (898 K) and residence time $\tau$=1 second, for a propane conversion of x=46% and propylene yield of y=42%

Activity Parameter=35,028

Selectivity Parameter=0.23

Characterization of the catalyst is conducted in the absence of a diluent gas such as nitrogen, hydrogen, steam or helium.

Attrition Index: The attrition resistance of catalysts used in fluidized reactor systems are characterized by the Attrition Index determined by ASTM tests such as AJI—Air Jet Index which is the percent attrition loss at 5 hours (ASTM D5757—Standard Test Method for Determination of Attrition of FCC Catalysts by Air Jets).

Calcination Temperature—The term "calcination temperature" refers to the maximum temperature utilized as an intermediate step in the catalyst synthesis procedure intended to convert the metal salts to their oxide form.

Conversion—The term "conversion of a reactant" refers to the reactant mole or mass change between a material flowing into a reactor and a material flowing out of the reactor divided by the moles or mass of reactant in the material flowing into the reactor. For propane dehydrogenation, selectivity is the mass of propane reacted divided by the mass of propane fed.

"Particle size" is number average particle size, and, for non-spherical particles, is based on the largest dimension.

Pore size—Pore size relates to the size of a molecule or atom that can penetrate into the pores of a material. As used herein, the term "pore size" for zeolites and similar catalyst compositions refers to the Norman radii adjusted pore size well known to those skilled in the art. Determination of Norman radii adjusted pore size is described, for example, in Cook, M.; Conner, W. C., "How big are the pores of zeolites?" Proceedings of the International Zeolite Conference, 12th, Baltimore, Jul. 5-10, 1998; (1999), 1, pp 409-414.

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, 1998.

Regeneration Temperature—The catalyst may be regenerated under flowing air gas at elevated temperatures in order to remove heavier hydrocarbons (coke) from the active catalyst structure. The maximum temperature used in this step is referred to as the "regeneration temperature."

Residence Time ($\tau$)—Residence time is the time a substance is in the reaction vessel. It can be defined as the volume of the catalyst bed divided by the flow rate (by volume per second) of gases into the reactor. $\tau$=volume of Catalyst bed ($m^3$)/volumetric flow of reactants ($m^3$/s).

Selectivity—The term "selectivity" refers to the amount of production of a particular product (or products) as a percent of all products resulting from a reaction. For example, if 100 grams of products are produced in a reaction and 80 grams of olefins are found in these products, the selectivity to olefins amongst all products is 80/100=80%. Selectivity can be calculated on a mass basis, as in the aforementioned example, or it can be calculated on a molar basis, where the selectivity is calculated by dividing the moles a particular product by the moles of all products. Unless specified otherwise, selectivity is on a mass basis. For propane dehydrogenation, selectivity is the mass of propylene produced divided by the mass of all products.

Yield—The term "yield" is used herein to refer to the amount of a product flowing out of a reactor divided by the amount of reactant flowing into the reactor, usually expressed as a percentage or fraction. Mass yield is the mass of a particular product divided by the weight of feed used to prepare that product. When unspecified, "%" refers to mass % which is synonymous with weight %. Ideal gas behavior is assumed so that mole % is the same as volume % in the gas phase. For propane dehydrogenation, mass yield is the mass of propylene produced divided by the mass of propane fed. Mass yield of the inventive processes are preferably at least 50% in a single pass, preferably at least 70%.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components. As is standard terminology, "systems" include to apparatus and materials (such as reactants and products) and conditions within the apparatus.

DETAILED DESCRIPTION

The catalyst can be used as powder or pellet, or can be disposed on a substrate such as a reactor wall or on beads or other support. For example, the catalyst can be deposited on a silica powder. This is sometimes termed as a catalyst material "grafted" on a support.

The catalyst preferably comprises a stabilized titania support. Preferably, the titanium in the catalyst is chiefly in the form of anatase as determined by XRD. Typically, the catalyst (not including an optional support material) comprises from 10 to 95 wt % titania, preferably 50 to 95, or 70 to 95, or 80 to 93 wt % titania (calculated assuming all Ti is present as TiO2).

The titania is stabilized with a stabilizing element comprising zirconium, tungsten, or a rare earth element or combinations thereof. The rare earth element, if present, preferably includes Ce and/or Y. The stabilizing element(s) are preferably present in 0.1 to 25 wt % (based on the weight of the fully oxidized, oxide form of the stabilizer element, or 0.1 to 20 wt %, or 0.5 to 20, or 1.0 to 20, or 0.5 to 15, or 0.5 to 10, or 1.0 to 15, or 2.0 to 15, or 2.0 to 10, or 4.0 to 8.0 wt % (based on the elements weight).

The catalyst preferably contains zinc, preferably in the range of 0.1 to 10%, more preferably 1 to 10, or 2 to 8, or 3 to 7 wt %.

Preferably, the catalyst comprises a BET surface area of at least 1, or at least 5, or at least 20, or in the range of 1 to 50, or 1 to 35 m$^2$/g.

The invention includes methods of making the catalyst, methods of dehydrogenating a paraffin having 2-8 carbon atoms (preferably propane or isobutane). The invention also includes reaction systems comprising a reactor comprising any of the catalysts described herein, a product stream comprising a paraffin having 2-8 carbon atoms (preferably propane or isobutane) passing through the reactor and in contact with the catalyst, preferably at the temperature and rate conditions described herein.

In a preferred method, the catalyst is employed in the dehydrogenation of a paraffin having 2-8 carbon atoms (preferably propane or isobutane). For example, in some embodiments, the catalyst is exposed to a stream comprising at least 50 mol % propane. In some embodiments, the method is conducted with a product stream of paraffins at a space velocity of 0.1 to 10 hr$^{-1}$, or 0.5 to 5, or 0.5 to 2 hr$^{-1}$., and preferably at a temperature of 500 to 700 C. In some embodiments, the method is conducted for a continuous period of at least 1 second or from 1 second to 120 seconds without regeneration and with a stability such that the rate of dehydrogenation decreases by no more than 10% or no more than 5% or no more than 2% over the continuous period.

Surprisingly, we have discovered that a catalyst containing titania and zinc, and stabilized by Zr, W, and/or rare earth metals exhibits a surprisingly superior combination of activity, selectivity, and stability results under conditions of propane dehydrogenation.

The invention is further elucidated in the examples below. In some preferred embodiments, the invention may be further characterized by any selected descriptions from the examples, for example, within ±20% (or within ±10%) of any of the values in any of the examples, tables or figures; however, the scope of the present invention, in its broader aspects, is not intended to be limited by these examples.

Example 1

The starting material was titanium (IV) oxide obtained from BASF. An appropriate amount of Zinc Nitrate Hexahydrate salt was dissolved in deionized water at room temperature to make a 10 wt % Zinc Nitrate solution. This solution was then added dropwise to the titanium (IV) oxide support. The wet catalyst was then left to dry at room temperature overnight. The catalyst was then calcined in a muffle furnace at 600° C. for 4 hours. The final catalyst had 3 wt % Zinc by weight. This catalyst is designated as Catalyst A.

Example 2

The catalyst was prepared as in Example 1 using silica (SiO$_2$) obtained from Sigma Aldrich as the catalyst support. This catalyst is designated as Catalyst B.

Example 3

The catalyst was prepared as in Example 1 using ceria (CeO$_2$) obtained from Sigma Aldrich as the catalyst support. This catalyst is designated as Catalyst C.

Example 4

The catalyst was prepared as in Example 1 using gamma-alumina (.—Al$_2$O$_3$) obtained from Alfa Aesar as the catalyst support. This catalyst will be designated as Catalyst D.

Example 5

Propane dehydrogenation experiments were performed using a fixed-bed reactor such that the $d_T/d_P$>10 (ratio of diameter of reactor tube to diameter of catalyst particles) and $L/d_P$>50 (ratio of length of catalyst bed to diameter of catalyst particles) to ensure plug-flow behavior. The catalyst of interest was first loaded into a quartz glass lined reactor. The catalyst was activated in dry air at atmospheric pressure at a temperature of 600° C. for 4 hours. Following activation, the reactor was allowed to heat up to reaction temperature of 625° C., then purged with dry nitrogen for 0.5 hours. Propane was fed to the reactor at a WHSV equal to 1 hr$^{-1}$. The flow rate was controlled by a Brooks mass flow controller. Product samples taken 5 minutes after the start of reaction were analyzed on GCs having Petrocol DH and Plot Q columns. The catalyst was regenerated at 625° C. by first purging the reactor with nitrogen and then passing air over the catalyst. The results are shown in Table 1.

TABLE 1

| Catalyst # | Support | Activity Parameter | Selectivity Parameter |
|---|---|---|---|
| A | $TiO_2$ | 1850 | 0.245 |
| B | $SiO_2$ | 272 | 2.346 |
| C | $CeO_2$ | 467 | 2.331 |
| D | $\gamma\text{-}Al_2O_3$ | 2694 | 1.244 |

Results show that $TiO_2$ as the best support for propane dehydrogenation. However, none of these supports showed adequate catalyst stability required for commercial application.

Example 6

The starting material was titanium (IV) oxide obtained from Alfa-Aesar. An appropriate amount of Zinc Nitrate Hexahydrate salt was dissolved in deionized water at room temperature to make a 3 wt % Zinc Nitrate solution. This solution was then added dropwise to the titanium (IV) oxide support. The wet catalyst was then left to dry at room temperature overnight. The catalyst was then calcined in a muffle furnace at 600° C. for 4 hours. The final catalyst had 1 wt % Zinc by weight. This catalyst is designated as Catalyst E.

Example 7

The starting material was titanium (IV) oxide obtained from Alfa-Aesar. An appropriate amount of Zinc Nitrate Hexahydrate salt was dissolved in deionized water at room temperature to make a 6 wt % Zinc Nitrate solution. This solution was then added dropwise to the titanium (IV) oxide support. The wet catalyst was then left to dry at room temperature overnight. The catalyst was then calcined in a muffle furnace at 600° C. for 4 hours. The final catalyst had 2 wt % Zinc by weight.

This catalyst is designated as Catalyst F.

Example 8

The starting material was titanium (IV) oxide obtained from Alfa-Aesar. An appropriate amount of Zinc Nitrate Hexahydrate salt was dissolved in deionized water at room temperature to make a 9 wt % Zinc Nitrate solution. This solution was then added dropwise to the titanium (IV) oxide support. The wet catalyst was then left to dry at room temperature overnight. The catalyst was then calcined in a muffle furnace at 600° C. for 4 hours. The final catalyst had 3 wt % Zinc by weight.

This catalyst is designated as Catalyst G.

Example 9

The starting material was titanium (IV) oxide obtained from Alfa-Aesar. An appropriate amount of Zinc Nitrate Hexahydrate salt was dissolved in deionized water at room temperature to make a 12 wt % Zinc Nitrate solution. This solution was then added dropwise to the titanium (IV) oxide support. The wet catalyst was then left to dry at room temperature overnight. The catalyst was then calcined in a muffle furnace at 600° C. for 4 hours. The final catalyst had 4 wt % Zinc by weight.

This catalyst is designated as Catalyst H.

Example 10

Catalysts E, F, G and H were tested for propane dehydrogenation activity as described in Example 5. The results are shown in Table 2.

TABLE 2

| Catalyst # | Zinc Loading | Activity Parameter | Selectivity Parameter |
|---|---|---|---|
| E | 1 wt % | 2615 | 0.912 |
| F | 2 wt % | 1912 | 0.216 |
| G | 3 wt % | 3017 | 0.194 |
| H | 4 wt % | 5391 | 2.827 |

Results shown in Table 2 clearly show that catalyst G with 3 wt % Zn loading has desired characteristics of adequate activity and selectivity.

Example 11

The catalyst was prepared as in Example 6 with the only difference being the doping of the support with 10 wt % Cerium prior to addition of zinc nitrate. Titanium oxide support was doped with 10% Cerium as follows: A 10 wt % cerium nitrate hexahydrate aqueous solution was first added dropwise to the titanium oxide support. The wet catalyst was then left to dry at room temperature overnight and then calcined to 600° C. for 4 hours. The addition of Zinc to the resulting support was then followed as in example 1.

This catalyst is designated as Catalyst I.

Example 12

The catalyst was prepared as in Example 11 with the only difference being the titanium oxide support was doped with 10 wt % Lanthanum.

This catalyst will be designated as Catalyst J.

Example 13

The catalyst was prepared as in Example 11 with the only difference being the titanium oxide support was doped with 10 wt % Yttrium.

This catalyst will be designated as Catalyst K.

Example 14

Catalysts I, J and K were tested for propane dehydrogenation activity as described in Example 5. The results are shown in Table 3.

TABLE 3

| Catalyst # | Rare Earth | Activity Parameter | Stability Parameter |
|---|---|---|---|
| G | None | 2939 | 18.5E−03 |
| I | $CeO_2$ | 2752 | 1.9E−03 |
| J | $La_2O_3$ | 2443 | 7.5E−03 |
| K | $Y_2O_3$ | 2329 | 3.3E−03 |

Results shown in Table 3 show the benefit of adding a Rare Earth Oxide to $TiO_2$ for stabilizing catalyst activity.

Example 15

A composite support comprising of Titania, Zirconia and Silica with a $TiO_2:ZrO_2:SiO_2$ ratio of 18:1:1 by weight was synthesized using a sol-gel hydrolysis technique. The appropriate amounts of Titanium (IV) Iso-propoxide, Zirconium (IV) propoxide and Tetra ethyl orthosilicate were mixed in 2-Propanol. The mixture was kept stirred using a magnetic bar at room temperature. Warm 0.1 M $NH_4NO_3$ aqueous solution was then added to the alkoxide mixture for hydrolysis. The resulting hydrolyzed sol-gel was allowed to stand at room temperature overnight. The sol-gel was dried and calcined at 450° C. for 4 hours. 3% Zinc was added to support as described in Example 1. This catalyst will be designated as Catalyst L.

Example 16

The appropriate amount of Titanium Isopropoxide, Zirconia and Silica with a $TiO_2:ZrO_2:SiO_2$ ratio of 18:1:1 by weight were mixed in 2-Propanol. Silica gel (150 Angstrom pore size) was slowly poured into the solution. The slurry mixture was stirred for 24 hours at room temperature. At the end of 24 hours, the mixture was heated at 70° C. for 1 hour. After 1 hour of heating, the excess solvent was decanted and residual solvent was driven off under the vacuum. The grafted support was hydrolyzed at 40° C. overnight. The hydrolyzed support was calcined to a temperature of 550° C. for 4 hours. The final loading of $TiO_2$ on the silica support was 10 wt %. 3 wt % Zinc as an active metal was added to grafted support employing a wet impregnation technique as described in Example 1. This catalyst will be designated as Catalyst M.

Example 17

Catalysts L and M. were tested for propane dehydrogenation activity as described in Example 5. The results are shown in Table 4.

TABLE 4

| Catalyst # | Activity Parameter | Selectivity Parameter |
|---|---|---|
| L | 3017 | 0.194 |
| M | 2926 | 0.204 |

As evident from table 4, the performance of the hydrolyzed catalyst and the grafted catalyst are essentially the same despite the fact that the grafted catalyst contains >88% of inert material.

Example 18

24 gm of Titanium Tetrachloride and 1.7 gm of Zirconium Tetrachloride were dissolved in 500 ml of deionized chilled (5° C.) water. The solution was heated to 55° C. while stirring. When the desired temperature was reached, 2 molar aqueous solution of ammonium hydroxide was added to solution till it reached a pH of 7.3. The precipitate was filtered and dried overnight and then calcined to a temperature of 700° C. for 4 hours to produce the stabilized catalyst support. 0.34 gm of Zinc Nitrate Hexahydrate was dissolved in 2.5 grams of deionized water at room temperature. The solution was then added to 11 grams of the stabilized catalyst support dropwise. The wet catalyst was dried and calcined at 700° C. for 4 hours to give a Zn loading of 3 wt %.

This catalyst is designated as Catalyst N.

Example 19

2.6 gm of Zinc Nitrate Hexahydrate, 24 gm of Titanium Tetrachloride and 1.7 gm of Zirconium Tetrachloride inorganic salts were dissolved in 500 ml of deionized chilled (5° C.) water. The solution was heated to 55° C. while stirring. When the desired temperature was reached, 2 M aqueous solution of ammonium hydroxide was added to the inorganic salts solution dropwise until the solution reached a pH of 7.3. The precipitate was filtered and dried overnight and then calcined to a temperature of 700° C. for 4 hours to produce the mixed-metal oxide catalyst This catalyst is designated as Catalyst O.

Example 20

The catalyst was prepared as in Example 19 with the only difference being the amount of Zinc Nitrate Hexahydrate added was 1.3 gm.

This catalyst is designated as Catalyst P.

Example 21

The catalyst was prepared as in Example 19 with the only difference being the amount of Zinc Nitrate Hexahydrate added was 4.0 gm.

This catalyst is designated as Catalyst Q.

Example 22

The catalyst was prepared as in Example 19 with the only difference being the amount of Zinc Nitrate Hexahydrate added was 5.5 gm.

This catalyst is designated as Catalyst R.

Example 23

The catalyst was prepared as in Example 19 with the only difference being the amount of Zinc Nitrate Hexahydrate added was 8.8 gm.

This catalyst is designated as Catalyst S.

Catalysts J to N were tested for propane dehydrogenation following Example 5 with the only difference being the propane WHSV was 2/hr. The results are shown in the Table 5.

TABLE 5

| Catalyst | Zinc Loading (wt %) | Activity Parameter | Selectivity Parameter | Stability Parameter |
|---|---|---|---|---|
| O | 5% | 28864.2 | 0.19 | 0 |
| P | 2.5% | 27930.21 | 0.41 | Not measured |
| Q | 7.5% | 21791.86 | 0.49 | Not measured |
| R | 10% | 27011.41 | 0.44 | Not measured |
| S | 15% | 14768.42 | 1.05 | Not measured |

The results show that excessive Zn loading can lead to inferior catalyst performance.

Example 24

2.6 gm of Zinc Nitrate Hexahydrate, 22 gm of Titanium Oxy-Sulfate and 1.7 gm of Zirconium Tetrachloride inorganic salts were dissolved in 500 ml of deionized water. The salt solution was heated to 55° C. while stirring. When the desired temperature was reached, 2 molar aqueous solution of ammonium hydroxide was added to the inorganic salts solution dropwise till the precipitate reached the pH of 7.3. The precipitate was filtered and dried overnight and then calcined to a temperature of 700° C. for 4 hours to produce the mixed-metal oxide catalyst. This catalyst is designated as Catalyst T.

Example 25

The catalyst was prepared as in Example 24 with the only difference being amount of Zinc Nitrate Hexahydrate added was 1.3 gm. This catalyst is designated as Catalyst U.

Example 26

The catalyst was prepared as in Example 24 with the only difference being amount of Zinc Nitrate Hexahydrate added was 4.0 gm. This catalyst is designated as Catalyst V.

Example 27

The catalyst was prepared as in Example 24 with the only difference being amount of Zinc Nitrate Hexahydrate added was 5.5 gm. This catalyst is designated as Catalyst W.

Example 28

The catalyst was prepared as in Example 24 with the only difference being amount of Zinc Nitrate Hexahydrate added was 8.8 gm. This catalyst is designated as Catalyst X.

Example 29

The catalyst was prepared as in Example 24 with the only difference being the bulk catalyst was washed with dilute $NH_4OH$ solution followed by dilute $NH_4NO_3$ solution for 30 minutes at room temperature. This catalyst is designated as Catalyst AI. The catalyst was submitted for BET analysis.

Catalysts T, U, W and AI were tested for propane dehydrogenation following Example 5 with the only difference being the propane WHSV was 2/hr. The results are shown in Table 6.

TABLE 6

| Catalyst | Zinc Loading (wt %) | Activity Parameter | Selectivity Parameter |
| --- | --- | --- | --- |
| T | 5% | 25217.45 | 0.5 |
| U | 2.5% | 19352.41 | 0.4 |
| W | 10% | 5329.02 | 13.71 |
| AI | 33 | 32762.64 | 0.15 |

The results indicate that washing the precipitate with ammonium nitrate and ammonium hydroxide solutions significantly improve catalyst performance.

Example 30

2.4 gm of Zinc Nitrate Hexahydrate and 22 gm of Titanium Oxy-Sulfate inorganic salts were dissolved in 500 ml of deionized water. The salt solution was heated to 55° C. while stirring. When the desired temperature was reached, 2 molar aqueous solution of ammonium hydroxide was added to the inorganic salts solution dropwise till the precipitate reached the pH of 7.3. The precipitate was filtered, washed with 0.1 M NH4OH for 30 minutes at room temperature followed by 0.25 M NH4NO3 wash for 30 minutes at room temperature. The catalyst was dried overnight and then calcined to a temperature of 700° C. for 4 hours to produce the mixed-metal oxide catalyst. This catalyst is designated as Catalyst AJ. The catalyst was submitted for BET analysis

Example 31

Commercially available Zinc Orthotitanate ($ZnO.TiO_2$) was obtained from Alfa Aesar. The catalyst was activated in situ at 450° C. overnight. The catalyst was tested for propane dehydrogenation reaction following similar operating condition as tested for other in-home synthesized catalysts. This catalyst is designated as Catalyst AK. The catalyst was submitted for BET analysis.

Example 32

The starting material was Tungsten (5 wt % $WO_3$) stabilized titanium (IV) oxide obtained from Cristal. An appropriate amount of Zinc Nitrate Hexahydrate salt was dissolved in deionized water at room temperature to make a 10 wt % Zinc Nitrate solution. This solution was then added dropwise to the titanium (IV) oxide support. The wet catalyst was then left to dry at room temperature overnight. The catalyst was then calcined in a muffle furnace at 700° C. for 4 hours. The final catalyst had 3 wt % Zinc by weight. This catalyst is designated as Catalyst AL.

Catalysts AJ to AL were tested for propane dehydrogenation following Example 5 with the only difference being the propane WHSV was 2/hr. The results are shown in the table 7. below:

TABLE 7

| Catalyst | BET surface area ($m^2$/gm) | Activity Parameter | Selectivity parameter |
| --- | --- | --- | --- |
| AJ | 8 | 14768.42 | 0.68 |
| AK | <1 | 1721.1 | 28.52 |
| AL | 87.2 | 35028 | 0.25 |

The data shows that the surface areas of $TiO_2$ supports drop significantly when raised to temperatures in excess of 600° C. without the presence of stabilizers such as $WO_3$ or $ZrO_2$.

Example 33

Figure 2:
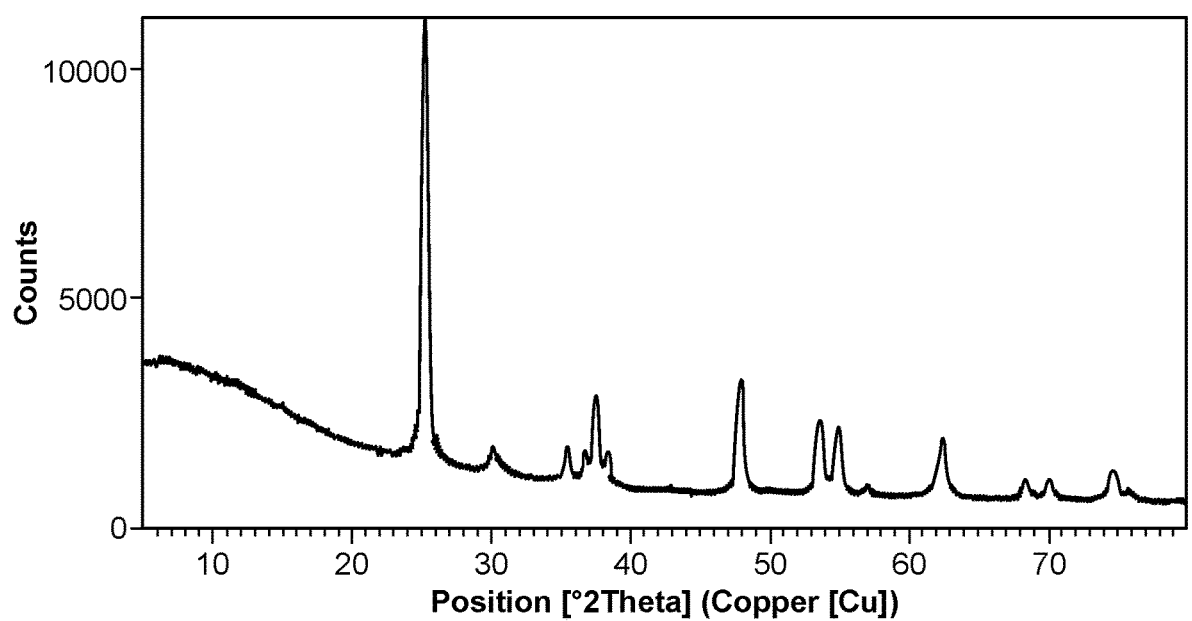
FIG. 2 shows an x-ray diffraction spectrum (XRD) of a $ZrO_2$ doped $TiO_2$ support; sample AI in the Examples section.

Sample AI was submitted for XRD analysis to determine the crystalline phases present. Results are shown in FIG. 2. Based on comparison with $TiO_2$ samples, the results show the presence of anatase phase as the major component in sample AI.

Example 34

Figure 3:
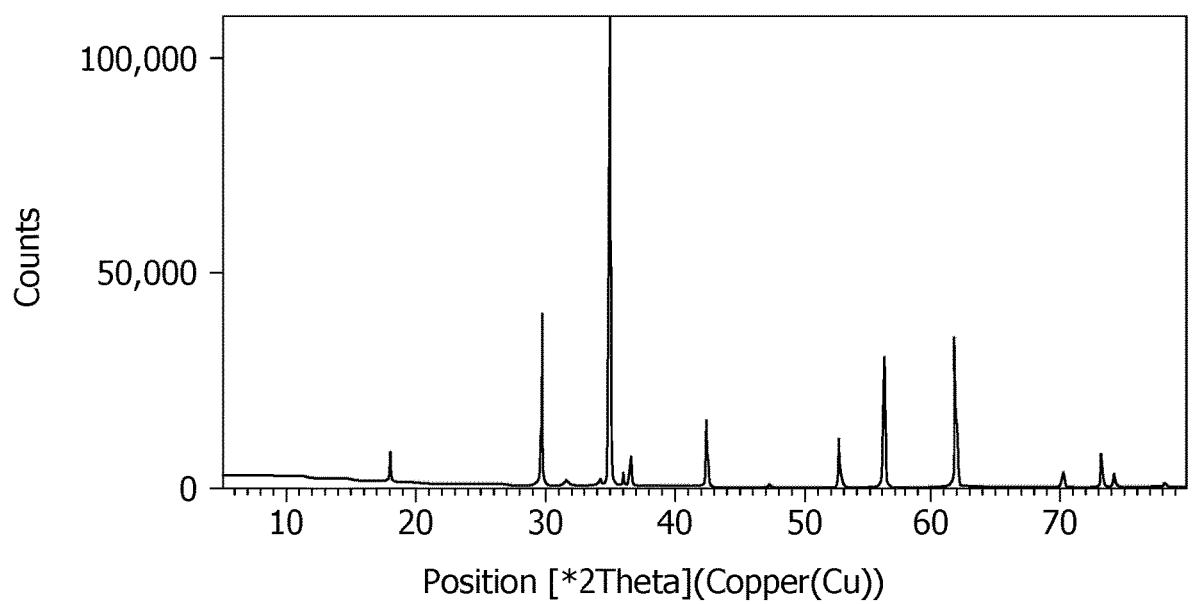
FIG. 3 shows an XRD of commercial $ZnO.TiO_2$ sample, AK.

Sample AI was submitted for XRD analysis to determine the crystalline phases present. Results are shown in FIG. 3. Based on XRD comparison with Zinc-Titanate samples, the results show the presence of ZnO—$TiO_2$ as the major component in sample AK.

The XRD data show the presence of anatase phase for the ZrO2 doped TiO2 support while the commercial ZnO.TiO2 shows clearly the presence of Zinc Titanate Phase.

What is claimed:

1. A mixed-metal oxide catalyst suitable for the dehydrogenation of paraffins having 2-8 carbon atoms comprising oxides of Transition Metals selected from the group of copper (Cu), iron (Fe), manganese (Mn), niobium (Nb) and zinc (Zn) as the active catalytic species wherein the active species makes up 0.1 to 20 wt % of the total weight of the catalyst, oxides of aluminum (Al), silicon (Si), titanium (Ti) and zirconium (Zr) or mixtures thereof as the catalyst support wherein the catalyst support makes up 10 to 90 wt % of the total weight of the catalyst, and oxides of Rare Earth metals as catalyst stabilizers selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), and yttrium (Y) wherein the catalyst stabilizer makes up 0.1 to 20 wt % of the total weight of the catalyst, and characterizable by
- a. Activity Parameter >1500,
- b. Selectivity Parameter <0.2, and
- c. Stability parameter <0.005 measured using a test where the metal oxide catalyst is loaded in a fixed-bed reactor such that the $50>d_T/d_P>10$ (diameter of tube to diameter of catalyst particles) and $200>L/d_P>50$ (length of catalyst bed to diameter of catalyst particles) and $2>d_P>0.5$ mm exposed to a feed stream comprising of propane at a temperature of 625° C., atmospheric pressure and a feed rate of 1 hr$^{-1}$ weight hourly space velocity.

2. A mixed metal oxide catalyst suitable for the dehydrogenation of paraffins having 2-8 carbon atoms with a catalyst composition of the general formula (AC) (CS) (ST) wherein
- a) AC represents oxides of Transition Metals selected from the group of copper (Cu), iron (Fe), manganese (Mn), niobium (Nb) and zinc (Zn) or mixtures thereof,
- b) CS represents oxides of aluminum (Al), silicon (Si), and titanium (Ti) or mixtures thereof,
- c) ST represents oxides of Rare Earth metals selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y), tungsten (W), zirconium (Zr), or mixtures thereof, and characterizable by a Activity Parameter >1500, Selectivity Parameter <0.2 and a stability parameter <0.005 using a test where the mixed metal oxide catalyst is loaded in a fixed-bed reactor such that the $50>dT/dP>10$ (diameter of tube to diameter of catalyst particles) and $200>L/dP>50$ (length of catalyst bed to diameter of catalyst particles) and $2>dP>0.5$ mm exposed to a feed stream of propane at a temperature of 625° C., atmospheric pressure and a feed rate of 1 hr$^{-1}$ or 2 hr$^{-1}$ weight hourly space velocity.

3. The catalyst composition according to claim 2 wherein the catalyst stabilizer makes up 1 to 15 wt % of the total weight of the catalyst.

4. The catalyst composition according to claim 2 wherein the catalyst stabilizer makes up 1 to 10 wt % of the total weight of the catalyst.

5. The catalyst composition of claim 2, wherein said catalyst composition has less than 100 ppm by weight of either platinum (Pt) or chromium (Cr).

6. The catalyst composition of claim 2 wherein the BET surface area >30 m$^2$/g.

7. A mixed metal oxide catalyst comprising a catalyst composition of the general formula (AC) (CS) (ST) (MS) wherein
- a) AC (Active Catalyst) represents oxides of Transition Metals selected from the group of copper (Cu), iron (Fe), manganese (Mn), niobium (Nb) and zinc (Zn) or mixtures thereof,
- b) CS (Catalyst Support) represents oxides of aluminum (Al), silicon (Si), and titanium (Ti) or mixtures thereof,
- c) ST (Support Stabilizer) represents oxides of metals selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y) Tungsten (W) and zirconium (Zr) or mixtures thereof,
- d) MS (Mechanical Stabilizer) represents porous spheres selected from the group of alumina, silica, titania, zirconia, kaolin, meta-kaolin, bentonite, attapulgite, or mixtures thereof;

and characterizable by a Activity Parameter >1500, Selectivity Parameter <0.5 and a stability parameter <0.005 using a test where the mixed metal oxide catalyst is loaded in a fixed-bed reactor such that the $50>dT/dP>10$ (diameter of tube to diameter of catalyst particles) and $200>L/dP>50$ (length of catalyst bed to diameter of catalyst particles) and $2>dP>0.5$ mm exposed to a feed stream of propane at a temperature of 625° C., atmospheric pressure and a feed rate of 2 hr$^{-1}$ weight hourly space velocity.

8. The catalyst of claim 1 wherein the active species makes up 0.1 to 7.5 wt % of the total weight of the catalyst.

9. The catalyst of claim 1 wherein the catalyst support makes up 50 to 80 wt % of the total weight of the catalyst.

10. The catalyst of claim 1 wherein the catalyst stabilizer makes up 1 to 10 wt % of the total weight of the catalyst.

11. The catalyst composition of claim 1, wherein said catalyst composition has less than 100 ppm by weight of either platinum (Pt) or chromium (Cr).

12. The catalyst composition of claim 1 wherein the BET surface area >30 m$^2$/g.

13. The mixed metal oxide catalyst of claim 7 wherein the catalyst support comprises a mesoporous bead.

14. The mixed metal oxide catalyst of claim 1 in the form of particles wherein the number average particle size is in the range of 30-3000 micrometers.

15. The mixed metal oxide catalyst of claim 7 wherein the active catalyst species makes up 0.1 to 7.5 wt % of the total weight of the catalyst; wherein the catalyst support makes up 20 to 90 wt % of the total weight of the catalyst; and wherein the catalyst stabilizer makes up 1 to 15 wt % of the total weight of the catalyst.

16. The mixed metal oxide catalyst of claim 1 wherein the active catalyst comprises zinc and the catalyst support comprises titania.

17. The mixed metal oxide catalyst of claim 7 wherein the active catalyst comprises zinc and the catalyst support comprises titania.

* * * * *